United States Patent
Matsunaga et al.

(10) Patent No.: US 9,598,382 B2
(45) Date of Patent: Mar. 21, 2017

(54) METHOD FOR PRODUCING PURIFIED COMPOUND

(71) Applicant: SUMITOMO CHEMICAL COMPANY, LIMITED, Tokyo (JP)

(72) Inventors: Tadafumi Matsunaga, Oita (JP); Hiromi Kaise, Takarazuka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 0 days.

(21) Appl. No.: 15/114,557

(22) PCT Filed: Dec. 25, 2014

(86) PCT No.: PCT/JP2014/084753
§ 371 (c)(1),
(2) Date: Jul. 27, 2016

(87) PCT Pub. No.: WO2015/115021
PCT Pub. Date: Aug. 6, 2015

(65) Prior Publication Data
US 2016/0347726 A1     Dec. 1, 2016

(30) Foreign Application Priority Data

Jan. 29, 2014 (JP) .................................. 2014-014031

(51) Int. Cl.
*C07D 265/36* (2006.01)

(52) U.S. Cl.
CPC .................. *C07D 265/36* (2013.01)

(58) Field of Classification Search
CPC .................................................. C07D 265/36
USPC ....................................................... 544/105
See application file for complete search history.

(56) References Cited

U.S. PATENT DOCUMENTS

| 4,803,270 A | 2/1989 | Takemoto |
| 5,247,082 A | 9/1993 | Matsumoto et al. |
| 5,256,822 A | 10/1993 | Takemoto et al. |

FOREIGN PATENT DOCUMENTS

| JP | 62-212375 A | 9/1987 |
| JP | 3-20247 A | 1/1991 |
| JP | 4-134052 A | 5/1992 |
| JP | 5-97826 A | 4/1993 |
| JP | 5-97848 A | 4/1993 |
| JP | 5-155869 A | 6/1993 |
| JP | 5-213844 A | 8/1993 |
| JP | 5-262704 A | 10/1993 |

OTHER PUBLICATIONS

International Preliminary Report on Patentability and Written Opinion of the International Searching Authority (Forms PCT/IB/373 and PCT/ISA/237) dated Aug. 2, 2016, for International Application No. PCT/JP2014/084753.
International Search Report (Form PCT/SA/210) dated Feb. 24, 2015, for International Application No. PCT/JP2014/084753.
Smith et al., "Chapter 16-2 Hydrolysis of the Carbon-Nitrogen Double Bond," March's Advances Organic Chemistry Reactions, Mechanisms, and Structure, 5th Edition, 2001, 4 pgs.

*Primary Examiner* — Brenda Coleman
(74) *Attorney, Agent, or Firm* — Birch, Stewart, Kolasch & Birch, LLP

(57) ABSTRACT

A method for producing a purified compound represented by the formula (II), comprising; obtaining a reaction mixture containing a compound represented by the formula (I) from a crude compound represented by the formula (II) such as reacting the crude compound with a ketone compound, and reacting the obtained reaction mixture or a solution by filtering thus obtained reaction mixture containing the compound represented by the formula (I) with water.

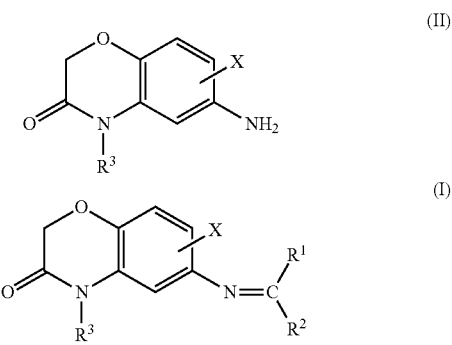

2 Claims, No Drawings

METHOD FOR PRODUCING PURIFIED COMPOUND

TECHNICAL FIELD

The present invention relates to a method for producing a purified compound.

BACKGROUND ART

Patent Document 1 describes that 6-amino-7-fluoro-2H-1,4-benzoxazin-3(4H)-one, as an intermediate of 2-(7-fluoro-4-propargyl-2H-1,4-benzoxazin-3(4H)-on-6-yl)-4,5,6,7-tetrahydroisoindole, is useful as intermediate as a herbicide.

PRIOR ART DOCUMENT PATENT DOCUMENT

Patent Document 1: Japanese Laid-Open Patent Application Publication No. 5-97826

SUMMARY OF INVENTION

Problems to be Solved by The Invention

A method for producing a compound represented by the formula (II) typically such as 6-amino-7-fluoro-2H-1,4-benzoxazin-3(4H)-one with high purity are required.

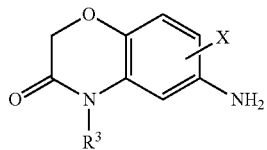

wherein $R^3$ represents a hydrogen atom, an alkyl group, an alkenyl group, or an alkynyl group, and X represents a halogen atom.

Means for Solving Problems

The present invention includes the following aspects of the invention.

[1] A method for producing a purified compound represented by the formula (II), comprising obtaining a reaction mixture containing a compound represented by the formula (I) from a crude compound represented by the formula (II), and reacting the obtained reaction mixture containing the compound represented by the formula (I) with water:

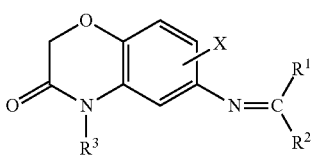

wherein $R^1$ and $R^2$ each independently represent an alkyl group, or $R^1$ and $R^2$ are bonded to each other to form a ring structure with a carbon atom to which $R^1$ and $R^2$ are bonded, $R^3$ represents a hydrogen atom, an alkyl group, an alkenyl group, or an alkynyl group, and X represents a halogen atom,

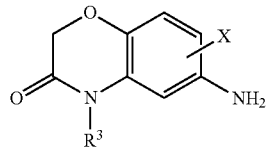

wherein $R^3$ and X represent the same meanings as above.

[2] The production method as described in [1], comprising obtaining the reaction mixture containing the compound represented by the formula (I) from the crude compound represented by the formula (II), filtering the obtained reaction mixture containing the compound represented by the formula (I), and reacting thus obtained solution with water.

DESCRIPTION OF EMBODIMENTS

Examples of the alkyl group in $R^1$ and $R^2$ include an alkyl group having 1 to 6 carbon atoms, such as a methyl group, an ethyl group, an n-propyl group, an isopropyl group, an n-butyl group, a sec-butyl group, a tert-butyl group, an isobutyl group, an n-pentyl group, and an n-hexyl group, and the alkyl group is preferably an alkyl group having 1 to 5 carbon atoms, and more preferably a methyl group or an isobutyl group.

Examples of the ring structure formed by the mutual bonding of $R^1$ and $R^2$ in combination with a carbon atom to which $R^1$ and $R^2$ are bonded include a cyclohexane ring and a cyclopentane ring.

Examples of the alkenyl group in $R^3$ include an alkenyl group having 2 to 6 carbon atoms, such as a vinyl group and an allyl group, and the alkenyl group is preferably an alkenyl group having 2 to 4 carbon atoms, and more preferably an allyl group.

Examples of the alkynyl group in $R^3$ include an alkynyl group having 2 to 6 carbon atoms, such as an ethynyl group and a 2-propynyl group, and the alkynyl group is preferably an alkynyl group having 2 to 4 carbon atoms, and more preferably a 2-propynyl group.

$R^3$ is preferably a hydrogen atom.

Examples of the halogen atom in X include a fluorine atom, a chlorine atom, a bromine atom, and an iodine atom, and the halogen atom is preferably a fluorine atom.

X is preferably bonded at the 7-position and a fluorine atom is preferably bonded at the 7-position.

Examples of the compound represented by the formula (II) (hereinafter sometimes referred to as a "compound (II)") include 6-amino-7-fluoro-2H-1,4-benzoxazin-3(4H)-one.

The crude compound (II) can be produced according to the method described in Japanese Patent Application Laid-Open No. 62-212375, for example. The purity of the crude compound (II) is usually from 80% to 95%.

Examples of the compound represented by the formula (I) (hereinafter sometimes referred to as a "compound (I)") include 6-(1,3-dimethylbutylideneamino)-7-fluoro-2H-1,4-benzoxazin-3(4H)-one and 6-(1-methylethylideneamino)-7-fluoro-2H-1,4-benzoxazin-3(4H)-one.

The compound (I) is preferably obtained by reacting a crude compound (II) with a ketone compound. The reaction of the crude compound (II) with the ketone compound is usually carried out by mixing the crude compound (II) with the ketone compound. The reaction is preferably carried out in the presence of an acid. Further, the reaction may also be carried out in the presence of a solvent.

The reaction temperature is usually from 60° C. to 200° C., and preferably from 70° C. to 150° C.

Examples of the ketone compound include acetone, methyl ethyl ketone, methyl isobutyl ketone, diethyl ketone, dibutyl ketone, cyclopentanone, and cyclohexanone, and the ketone compound is preferably methyl isobutyl ketone.

The amount of the ketone compound to be used is usually from 1 mole to 100 moles with respect to 1 mole of the crude compound (II). The ketone compound may be used in combination with a solvent.

Examples of the acid include hydrochloric acid, sulfuric acid, acetic acid, p-toluenesulfonic acid, and methanesulfonic acid, and the acid is preferably p-toluenesulfonic acid.

The amount of the acid to be used is usually from 0.001 moles to 0.01 moles with respect to 1 mole of the crude compound (II).

Examples of the solvent include an aromatic compound such as toluene and xylene; a halogen compound such as methylene chloride, an aliphatic hydrocarbon compound such as hexane and heptane; and a mixture thereof.

The amount of the solvent to be used is usually from 1 part by weight to 50 parts by weight, preferably from 1 part by weight to 30 parts by weight, and more preferably from 1 part by weight to 20 parts by weight, with respect to 1 part by weight of the crude compound (II).

A reaction mixture obtained by reacting the compound (II) with the ketone compound may be, for example, concentrated and filtered to extract a compound (I). The obtained reaction mixture may be reacted with water and the compound (I) may be extracted and reacted with water. Preferably, the obtained reaction mixture is filtered and thus obtained solution is reacted with water.

The reaction of the compound (I) with water is preferably carried out by mixing the compound (I) and water. The mixing is preferably carried out by adding water to the compound (I).

The reaction of the compound (I) with water is preferably carried out in the presence of an acid or a solvent.

The reaction temperature is usually from 0° C. to 100° C., and preferably from 20° C. to 80° C.

The reaction may be carried out under a nitrogen atmosphere. Further, the reaction may be carried out under reduced pressure.

The amount of water to be used is usually from 1 mole to 100 moles, and preferably from 1 mole to 10 moles, with respect to 1 mole of the compound (I).

Examples of the acid include those as mentioned above.

The amount of the acid to be used is usually from 0.001 moles to 1 mole, and preferably from 0.001 moles to 0.01 moles, with respect to 1 mole of the compound (I).

Examples of the solvent include acetone, methanol, ethanol, isopropylalcohol, toluene, methyl ethyl ketone, and methyl isobutyl ketone, and the solvent is preferably methyl isobutyl ketone.

The amount of the solvent to be used is usually from 1 part by weight to 50 parts by weight, preferably 1 part by weight to 30 parts by weight, and more preferably 1 part by weight to 20 parts by weight, with respect to 1 part of by weight of the compound (I).

A reaction mixture obtained by reacting the compound (I) with water may be, for example, concentrated and filtered to extract a purified compound (II).

The purified compound (II) has higher purity than the crude compound (II). The purity of the purified compound (II) is usually 96% or more.

According to the present invention, the compound represented by the formula (II) having high purity can be produced.

EXAMPLES

Hereinafter, the present invention will be described in more details with reference to Examples. Further, the purity is determined from a ratio of a peak area of a predetermined compound to a total sum of peak areas excluding peaks of solvents, from the analysis results of high performance liquid chromatography.

Example 1

Under nitrogen atmosphere, 25 g (purity 95.3%) of crude 6-amino-7-fluoro-2H-1,4-benzoxazin-3(4H)-one, 190 g of methyl isobutyl ketone, and 0.1 g of p-toluenesulfonic acid were put into a flask. The mixture was heated to 110° C. under reduced pressure, followed by refluxing and dehydrating for 5 hours. After the dehydration, 86 g of methyl isobutyl ketone was evaporated, and further filtered and washed to obtain a solution (content of 16.0%, yield of 100%) of 6-(1,3-dimethylbutylideneamino)-7-fluoro-2H-1,4-benzoxazin-3(4H)-one in methyl isobutyl.

126 g of the obtained solution was put into a flask and warmed to 100° C. under reduced pressure, and 58 g of methyl isobutyl ketone was evaporated. To the obtained mixture was added 4 g of water at 70° C., and the mixture was reacted and concentrated under reduced pressure concentrated. The obtained suspension was filtered, washed with methanol and water, and purified to obtain 6-amino-7-fluoro-2H-1,4-benzoxazin-3(4H)-one (purity of 99.4%, yield of 97%).

INDUSTRIAL APPLICABILITY

According to the present invention, a compound represented by the formula (II) having high purity can be produced.

The invention claimed is:

1. A method for producing a purified compound represented by the formula (II), comprising
obtaining a reaction mixture containing a compound represented by the formula (I) from a crude compound represented by the formula (II), and reacting the obtained reaction mixture containing the compound represented by the formula (I) with water:

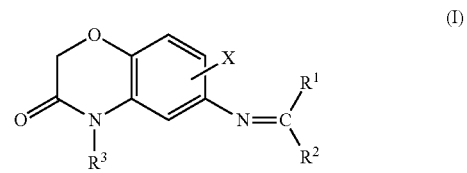

(I)

wherein $R^1$ and $R^2$ each independently represent an alkyl group, or $R^1$ and $R^2$ are bonded to each other to form a ring structure with a carbon atom to which $R^1$ and $R^2$ are bonded, $R^3$ represents a hydrogen atom, an alkyl group, an alkenyl group, or an alkynyl group, and X represents a halogen atom,

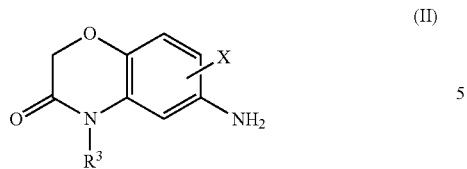 (II)

wherein R³ and X represent the same meanings as above.

2. The production method according to claim 1, comprising obtaining the reaction mixture containing the compound represented by the formula (I) from the crude compound represented by the formula (II), filtering the obtained reaction mixture containing the compound represented by the formula (I), and reacting thus obtained solution with water.

* * * * *